United States Patent
Chan et al.

(10) Patent No.: US 12,226,218 B2
(45) Date of Patent: Feb. 18, 2025

(54) ELECTRONIC DEVICE AND METHOD FOR PREDICTING BLOCKAGE OF CORONARY ARTERY

(71) Applicants: National Health Research Institutes, Miaoli County (TW); Chang Gung Memorial Hospital, Keelung, Keelung (TW); Acer Medical Inc., New Taipei (TW); Acer Incorporated, New Taipei (TW)

(72) Inventors: Yun-Hsuan Chan, New Taipei (TW); Chun-Hsien Li, New Taipei (TW); Jun-Hong Chen, New Taipei (TW); Tsung-Hsien Tsai, New Taipei (TW); Ting-Fen Tsai, Miaoli County (TW); Chi-Hsiao Yeh, Keelung (TW)

(73) Assignees: ACER INCORPORATED, New Taipei (TW); National Health Research Institutes, Miaoli County (TW); CHANG GUNG MEMORIAL HOSPITAL, KEELUNG, Keelung (TW); ACER MEDICAL INC., New Taipei (TW)

( * ) Notice: Subject to any disclaimer, the term of this patent is extended or adjusted under 35 U.S.C. 154(b) by 322 days.

(21) Appl. No.: 17/233,569

(22) Filed: Apr. 19, 2021

(65) Prior Publication Data

US 2022/0202339 A1    Jun. 30, 2022

(30) Foreign Application Priority Data

Dec. 28, 2020  (TW) ................................. 109146425

(51) Int. Cl.
  *A61B 5/355*   (2021.01)
  *A61B 5/00*    (2006.01)
  *A61B 5/341*   (2021.01)
  *A61B 5/352*   (2021.01)
  *A61B 5/353*   (2021.01)

(52) U.S. Cl.
  CPC .............. *A61B 5/341* (2021.01); *A61B 5/352* (2021.01); *A61B 5/353* (2021.01); *A61B 5/355* (2021.01); *A61B 5/726* (2013.01); *A61B 5/7275* (2013.01)

(58) Field of Classification Search
  CPC ....................................................... A61B 5/341
  (Continued)

(56) References Cited

U.S. PATENT DOCUMENTS 8,489,181 B1 *  7/2013  Schipper ................ A61B 5/341
                                                      600/509
2007/0233198 A1 * 10/2007  Ghanem ................ A61B 5/364
                                                      607/5

(Continued)

FOREIGN PATENT DOCUMENTS

CN    105792741    7/2016
CN    107174219    1/2019

(Continued)

OTHER PUBLICATIONS

Wikipedia, "Electrocardiography", Nov. 6, 2021, Available at: https://en.wikipedia.org/w/index.php?title=Electrocardiography&oldid=996488060.

(Continued)

*Primary Examiner* — Nicole F Lavert
(74) *Attorney, Agent, or Firm* — Edell, Shapiro & Finnan, LLC

(57) ABSTRACT

An electronic device and a method for predicting a blockage of a coronary artery are provided. The method includes: obtaining multiple pieces of electrocardiogram (ECG) data respectively corresponding to a coronary artery set; generating multiple first probabilities corresponding to the multiple pieces of electrocardiogram data respectively according to the multiple pieces of electrocardiogram data and a (Continued)

first phase model, generating a first determined result according to the multiple first probabilities, and selecting a first data subset corresponding to a first probability subset from the multiple pieces of electrocardiogram data in response to each one in the first data subset of the multiple first probabilities being greater than a first threshold; generating multiple second probabilities corresponding to the first data subset according to the first data subset and a second phase model, and generating a second determined result according to the multiple second probabilities.

9 Claims, 6 Drawing Sheets

(58) Field of Classification Search
USPC .......................................................... 600/512
See application file for complete search history.

(56) References Cited

U.S. PATENT DOCUMENTS

| | | | |
|---|---|---|---|
| 2015/0164453 A1* | 6/2015 | Choi | A61B 6/503 600/407 |
| 2017/0178403 A1* | 6/2017 | Krummen | A61B 5/7278 |
| 2017/0262733 A1* | 9/2017 | Gulsun | G06V 10/454 |
| 2020/0205745 A1 | 7/2020 | Khosousi et al. | |

FOREIGN PATENT DOCUMENTS

| | | |
|---|---|---|
| CN | 109377470 | 2/2019 |
| CN | 110251122 | 9/2019 |
| TW | 201023062 | 6/2010 |

OTHER PUBLICATIONS

Azam Davari Dolatabadi et al., "Automated diagnosis of coronary artery disease (CAD) patients using optimized SVM", Computer Methods and Programs in Biomedicine. Elsevier, Oct. 24, 2016, pp. 117-126.

Gautam Phadke et al., "Prediction of Coronary Artery Disease using Electrocardiography Machine Learning Approach", 2020 International Conference On Machine Learning and Cybernetics (ICMLC). IEEE., Dec. 2, 2020, pp. 175-180.

"Search Report of Europe Counterpart Application", issued on Nov. 16, 2021, p. 1-p. 14.

* cited by examiner

ELECTRONIC DEVICE AND METHOD FOR PREDICTING BLOCKAGE OF CORONARY ARTERY

CROSS-REFERENCE TO RELATED APPLICATION

This application claims the priority benefit of Taiwan application serial no. 109146425, filed on Dec. 28, 2020. The entirety of the above-mentioned patent application is hereby incorporated by reference herein and made a part of this specification.

BACKGROUND

Technical Field

The disclosure relates to an electronic device and a method for predicting a blockage of a coronary artery.

Description of Related Art

The mortality rate of cardiovascular diseases is increasing year by year. Common cardiovascular diseases include coronary artery disease (CAD) or atrial fibrillation. At present, many diagnosis tests are adopted for detecting cardiovascular diseases in the medical field, such as blood tests, electrocardiogram, or cardiac catheterization. The cause of coronary artery disease is that the coronary arteries surrounding the surface of the heart are too narrow or blocked, causing the arterial blood flow that supplies oxygen and nutrients to the heart to fail to function properly. Among the current diagnosis tests, cardiac catheterization is one of the most accurate methods for detecting coronary artery disease.

However, the cardiac catheterization is an invasive examination procedure, which has risks and may cause complications. Performing cardiac catheterization only on patients who need to be examined prevents not only the waste of medical costs but also subjecting the patients to risks. Therefore, the prediction of whether the coronary artery is blocked may help doctors determine whether the cardiac catheterization is needed in a more precise matter. Moreover, for doctors, the prediction of the position of a blocked coronary artery also contributes to a better understanding of the condition of the patients.

SUMMARY

The disclosure provides an electronic device and a method for predicting a blockage of a coronary artery, capable of predicting whether a coronary artery is blocked, the type of a blocked coronary artery, or the position of a blocked coronary artery.

In the disclosure, the electronic device for predicting a blockage of a coronary artery includes a processor, a storage medium, and a transceiver. The transceiver receives multiple pieces of electrocardiogram (ECG) data corresponding to a coronary artery set. The storage medium stores multiple modules. The processor is coupled to the storage medium and the transceiver and accesses and executes the multiple modules. The multiple modules include a first prediction module, a second prediction module, and an output module. The first prediction module generates at least one first probability vector corresponding to at least one first phase model according to the multiple pieces of electrocardiogram data and the at least one first phase model, a first determined result is generated according to the at least one first probability vector, and a first data subset corresponding to a first subset is selected from the multiple pieces of electrocardiogram data in response to each one in the first subset of the at least one first probability vector being greater than a first threshold. The first determined result indicates a probability of a blockage of the coronary artery set. The second prediction module generates at least one second probability vector corresponding to at least one second phase model according to the first data subset and the at least one second phase model, and a second determined result is generated according to the at least one second probability vector. The second determined result indicates a probability of a blockage of a first coronary artery in the coronary artery set. The output module outputs the first determined result and the second determined result through the transceiver.

In an embodiment of the disclosure, the second prediction module selects a second data subset corresponding to a second subset from the first data subset in response to each one in the second subset of the at least one second probability vector being greater than a second threshold. The multiple modules further include a third prediction module. The third prediction module generates at least one third probability vector corresponding to at least one third phase model according to the second data subset and the at least one third phase model, a third determined result is generated according to the at least one third probability vector. The third determined result indicates a probability of a first blockage position of the first coronary artery. The output module outputs the third determined result through the transceiver.

In an embodiment of the disclosure, the transceiver receives multiple pieces of second electrocardiogram data corresponding to the coronary artery set. The multiple pieces of electrocardiogram data correspond to a first lead. The multiple pieces of second electrocardiogram data correspond to a second lead. The first prediction module generates at least one fourth probability vector corresponding to the at least one first phase model according to the multiple pieces of second electrocardiogram data and the at least one first phase model, and the first determined result is generated according to the at least one first probability vector and the at least one fourth probability vector.

In an embodiment of the disclosure, the first prediction module selects a fourth data subset corresponding to a fourth subset from the multiple pieces of second electrocardiogram data in response to each one in the fourth subset of the at least one fourth probability vector being greater than the first threshold. The second prediction module generates at least one fifth probability vector corresponding to the at least one second phase model according to the fourth data subset and the at least one second phase model, and the second determined result is generated according to the at least one second probability vector and the at least one fifth probability vector.

In an embodiment of the disclosure, the second prediction module selects a fifth data subset corresponding to a fifth subset from the fourth data subset in response to each one in the fifth subset of the at least one fifth probability vector being greater than the second threshold. The third prediction module generates at least one sixth probability vector corresponding to the at least one third phase model according to the fifth data subset and the at least one third phase model, and the third determined result is generated according to the at least one third probability vector and the at least one sixth probability vector.

In an embodiment of the disclosure, the first prediction module performs a baseline wandering removal, a noise removal, and a wavelet transform on multiple pieces of training data to generate multiple pieces of first corrected training data, and the at least one first phase model is trained according to the multiple pieces of first corrected training data.

In an embodiment of the disclosure, the first prediction module trains the at least one first phase model according to at least one feature. The at least one feature is associated with at least one of the following: a P wave, a Q wave, a R wave, an S wave, and a T wave.

In an embodiment of the disclosure, the at least one first phase model, the at least one second phase model, and the at least one third phase model correspond to a machine learning algorithm.

In an embodiment of the disclosure, the first coronary artery comprises at least one of the following: a left main coronary artery, a left anterior descending (LAD) artery, a left circumflex (LCX) artery, and a right coronary artery.

A method for predicting a blockage of a coronary artery includes steps as follows: obtaining multiple pieces of electrocardiogram (ECG) data corresponding to a coronary artery set; generating multiple first probabilities respectively corresponding to the multiple pieces of electrocardiogram data according to the multiple pieces of electrocardiogram data and at least one first phase model, generating a first determined result according to the plurality of the first probabilities, and selecting a first data subset corresponding to a first probability subset from the multiple pieces of electrocardiogram data in response to each one in the first probability subset of the multiple first probabilities being greater than a first threshold, wherein the first determined result indicates a probability of a blockage of the coronary artery set; generating multiple second probabilities corresponding to the first data subset according to the first data subset and at least one second phase model, and generating a second determined result according to the multiple second probabilities, wherein the second determined result indicates a probability of a blockage of a first coronary artery in the coronary artery set; and outputting the first determined result and the second determined result.

Based on the above, in the disclosure, a machine learning model is adopted to predict the type of a blocked coronary artery or the blockage position of a coronary artery. Medical personnel may diagnose whether the subject suffers from coronary artery disease according to the determined results generated in the disclosure in a more precise matter.

DESCRIPTION OF THE EMBODIMENTS

Figure 1:
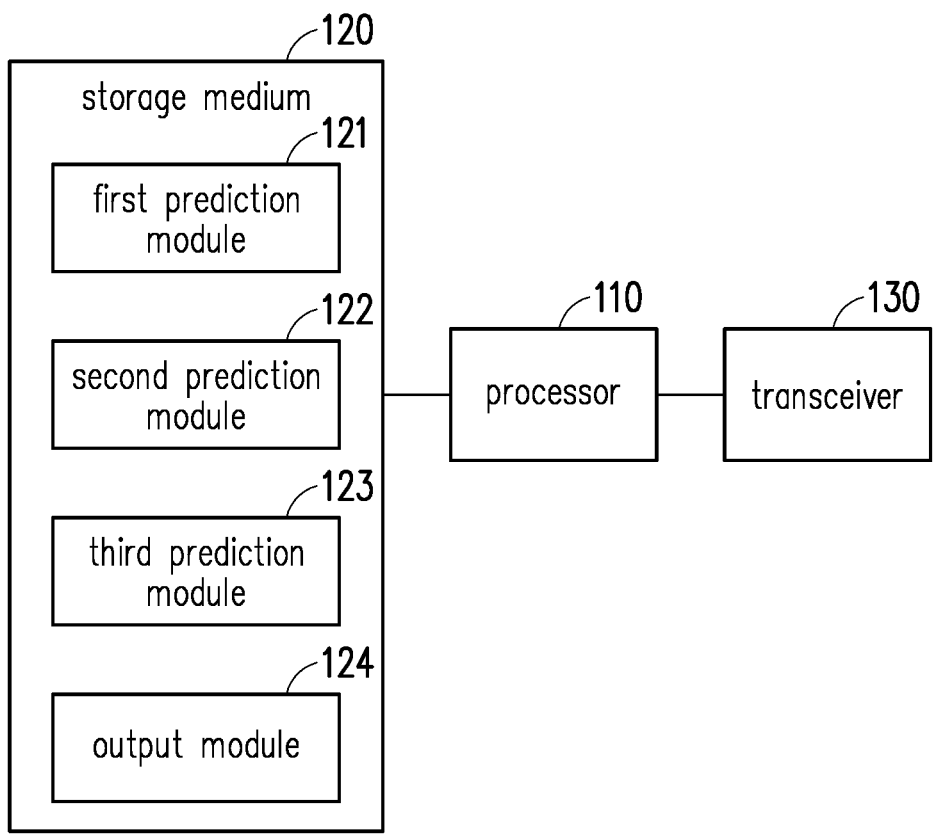
FIG. 1 illustrates a schematic view of an electronic device according to an embodiment of the disclosure.

In order to make the content of the disclosure comprehensible, embodiments are described in detail below. Moreover, whenever possible, the same reference numerals are used to represent the same or similar parts in the accompanying drawings and description.

FIG. 1 illustrates a schematic view of an electronic device 100 according to an embodiment of the disclosure. The electronic device 100 is adapted for predicting a blockage of a coronary artery. The electronic device 100 may include a processor 110, a storage medium 120, and a transceiver 130.

For example, the processor 110 is a central processing unit (CPU), or other programmable general-purpose or special-purpose micro control units (MCUs), a microprocessor, or a digital signal processor (DSP), a programmable controller, an application specific integrated circuit (ASIC), a graphics processing unit (GPU), an image signal processor (ISP), an image processing unit (IPU), an arithmetic logic unit (ALU), a complex programmable logic device (CPLD), a field programmable gate array (FPGA), other similar elements, or a combination thereof. The processor 110 may be coupled to the storage medium 120 and the transceiver 130, and access and execute multiple modules and various application programs stored in the storage medium 120.

For example, the storage medium 120 is any type of fixed or removable random access memories (RAMs), read-only memories (ROMs), or flash memories, a hard disk drive (HDD), a solid state drive (SSD), similar elements, or a combination thereof. The storage medium 120 is adapted to store multiple modules or various application programs that may be executed by the processor 110. In the embodiment, the storage medium 120 may store multiple modules including a first prediction module 121, a second prediction module 122, a third prediction module 123, and an output module 124, and the functions of which are illustrated in the subsequent paragraphs.

The transceiver 130 transmits and receives signals in a wireless or wired manner. The transceiver 130 may further perform operations, such as low noise amplification, impedance matching, frequency mixing, up or down frequency conversion, filtering, amplification, and the like.

Figure 2:
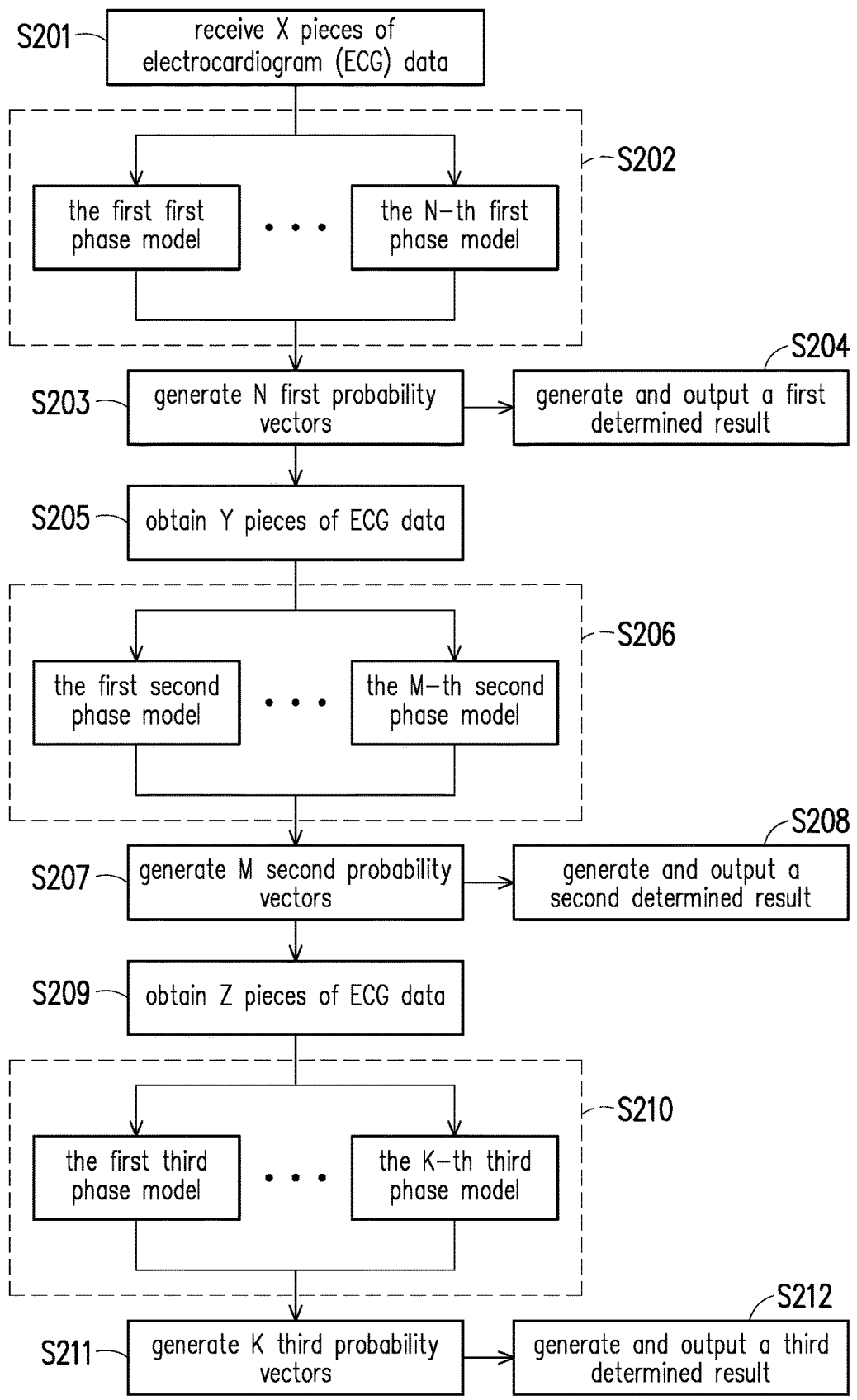
FIG. 2 illustrates a flowchart of a method for predicting a blockage of a coronary artery according to an embodiment of the disclosure.

FIG. 2 illustrates a flowchart of a method for predicting a blockage of a coronary artery according to an embodiment of the disclosure, and the method may be implemented by the electronic device 100 as shown in FIG. 1.

In step S201, the electronic device 100 may receive X pieces of electrocardiogram (ECG) data corresponding to the coronary artery set through the transceiver 130, where X may be any positive integer. The coronary artery set may include multiple coronary arteries, such as a left main (LM) artery, a left anterior descending (LAD) artery, a left circumflex (LCX) artery, and/or a right coronary artery (RCA).

In step S202 and step S203, the first prediction module 121 may generate at least one first probability vector corresponding to at least one first phase model according to the X pieces of ECG data and the at least one first phase model. The at least one first probability vector may include X first probabilities respectively corresponding to the X pieces of ECG data.

Specifically, in step S202, the first prediction module 121 may input X pieces of ECG data respectively into N first phase models, where N may be any positive integer. Next, in step S203, the N first phase models may generate N first probability vectors respectively according to the X pieces of ECG data. Each of the N probability vectors may include X first probabilities respectively corresponding to X pieces of ECG data.

The first phase model may be adapted to determine the probability of a blockage of any coronary artery in the coronary artery set according to the ECG data. After a piece of ECG data is input to the first phase model, the first phase model may output a first probability corresponding to the piece of ECG data. The first probability may represent the probability of the blockage of any coronary artery in the coronary artery set.

For example, the first phase model is a machine learning algorithm. For example, the machine learning algorithm corresponds to an algorithm, such as a random forest (RF) algorithm, a support vector machine (SVM) algorithm, an extreme gradient boosting (XGBoost) algorithm, or a deep learning algorithm, and the like, but the disclosure is not limited thereto. For example, the deep learning algorithm corresponds to an algorithm, such as a convolutional neural network (CNN) algorithm or a long short-term memory (LSTM) algorithm, but the disclosure is not limited thereto.

In an embodiment, the first prediction module 121 may train the first phase model according to multiple pieces of training data. Each of the multiple pieces of training data may include ECG data and a label indicating whether any coronary artery in the coronary artery set of the subject is blocked. Specifically, the first prediction module 121 may perform a baseline wandering removal, a noise removal, and a wavelet transform on the multiple pieces of training data to generate multiple pieces of first corrected training data. Then, the first prediction module 121 may train the first phase model according to the multiple pieces of training data.

In an embodiment, the first prediction module 121 may perform the baseline wandering removal on the multiple pieces of training data according to a cubic spline smoothing algorithm.

In an embodiment, the first prediction module 121 may perform the noise removal on the multiple pieces of training data according to a Butterworth filter.

In an embodiment, the first prediction module 121 may train one or more features in the training data to train the first phase model. For example, one or more features are associated with a P wave, a Q wave, a R wave, an S wave, or a T wave. For example, the features may include the standard deviation of the RR interval calculated from the R wave or the slope of the ST wave calculated from the S wave and the T wave, etc., but the disclosure is not limited thereto.

In step S204, the first prediction module 121 may generate a first determined result according to the N first probability vectors. The output module 124 may output the first determined result through the transceiver 130. The first determined result may include a probability S1 of the blockage of any coronary artery in the coronary artery set of the subject. For example, the first determined result may be the first probability of the blockage of the coronary artery set. After the doctor receives the first determined result from the electronic device 100 through the terminal device, the doctor may determine whether to perform a further examination on the coronary arteries of the subject according to the first determined result.

In an embodiment, the first prediction module 121 may calculate the probability S1 of the blockage of any coronary artery in the coronary artery set according to the following formula (1) and formula (2), where p1(i,j) is the i-th first probability in the j-th first probability vector in the N first probability vectors, and w1(j) is the weight of the j-th first phase model corresponding to the N first phase models. The first prediction module 121 may determine the weight corresponding to the first phase model according to the performance index of the first phase model. For example, in the N first phase models, if the performance index of the first phase model is greater than the performance index of the N-th first phase model, the first prediction module 121 may determine the weight w1(1) is greater than the weight w1(N). The performance index may correspond to a parameter in a confusion matrix, such as accuracy (ACC), precision, a recall rate, a false positive (FP), or an F1 score.

$$S1 = \sum_{j=1}^{N} \overline{p1(j)} * w1(j) \qquad (1)$$

$$\overline{p1(i,j)} = \frac{\sum_{i=1}^{X} p1(i,j)}{X} \qquad (2)$$

In step S205, the first prediction module 121 may select the first data subset corresponding to the first subset from the X pieces of ECG data in response to each one in the first subset of the first probability vectors (including one or more first probabilities included in the first probability vectors) being greater than a first threshold. When there are multiple first probability vectors, the first prediction module 121 may calculate the average first probability vector according to the multiple first probability vectors, and may select the first data subset corresponding to the first subset from the X pieces of ECG data in response to each one in the first subset of the average first probability vectors (including one or more average first probabilities included in the average first probability vector) being greater than the first threshold.

For example, if the first threshold is 30%, and Y of the X first probabilities of the first probability vectors are greater than 30%, where Y may be a positive integer less than or equal to X. Accordingly, the first prediction module 121 may select Y pieces of ECG data corresponding to the Y first probabilities from the X pieces of ECG data as the first data subset.

In step S206 and step S207, the second prediction module 122 may generate at least one second probability vector corresponding to at least one second phase model according to the first data subset (i.e., the Y pieces of ECG data) and the at least one second phase model. The at least one second probability vector may include Y second probabilities corresponding to the first data subset.

Specifically, in step S206, the second prediction module 122 may input the first data subset (i.e., the Y pieces of ECG data) into M second phase models, where M may be any positive integer. Then, in step S207, the M second phase models may generate M second probability vectors according to the first data subset. Each of the M second probability vectors may include Y second probabilities respectively corresponding to the Y pieces of ECG data.

The second phase model may be adapted to determine the probability of a blockage of a specific coronary artery in the coronary artery set according to the ECG data. For example, the second phase model may determine the probability of the blockage of the specific coronary artery in the left main coronary artery, the left anterior descending (LAD) artery, the left circumflex artery, and the right coronary artery according to the ECG data. After a piece of ECG data is input to the second phase model, the second phase model may output a second probability corresponding to the piece of ECG data. The second probability may represent the probability of the blockage of the specific coronary artery.

For example, the second phase model is a machine learning algorithm. For example, the machine learning algorithm corresponds to an algorithm, such as a random forest (RF) algorithm, a support vector machine (SVM) algorithm, an extreme gradient boosting (XGBoost) algorithm, or a deep learning algorithm, and the like, but the disclosure is not limited thereto. For example, the deep learning algorithm corresponds to an algorithm, such as a convolutional neural network (CNN) algorithm or a long short-term memory (LSTM) algorithm, but the disclosure is not limited thereto.

In an embodiment, the second prediction module 122 may train the second phase model according to multiple pieces of training data. Each of the multiple pieces of training data may include ECG data and a label indicating whether the specific coronary artery in the coronary artery set of the subject is blocked. Specifically, the second prediction module 122 may perform a baseline wandering removal, a noise removal, and a wavelet transform on the multiple pieces of training data to generate multiple pieces of second corrected training data. Then, the second prediction module 122 may train the second phase model according to the multiple pieces of second corrected training data.

In an embodiment, the second prediction module 122 may perform the baseline wandering removal on the multiple pieces of training data according to a cubic spline smoothing algorithm.

In an embodiment, the second prediction module 122 may perform the noise removal on the multiple pieces of training data according to a Butterworth filter.

In an embodiment, the second prediction module 122 may train one or more features in the training data to train the second phase model. For example, one or more features are associated with a P wave, a Q wave, a R wave, an S wave, or a T wave. For example, the features may include the standard deviation of the RR interval calculated from the R wave or the slope of the ST wave calculated from the S wave and the T wave, etc., but the disclosure is not limited thereto.

In step S208, the second prediction module 122 may generate a second determined result according to M second probability vectors. The output module 124 may output the second determined result through the transceiver 130. The second determined result may include a probability S2 of the blockage of the specific coronary artery in the coronary artery set of the subject.

In an embodiment, the second prediction module 122 may calculate the probability S2 of the blockage of the specific coronary artery in the coronary artery set according to the following formula (3) and formula (4), where p2(i,j) is the i-th second probability in the j-th second probability vector in the M second probability vectors, and w2(j) is the weight of the j-th second phase model corresponding to the M second phase models. The second prediction module 122 may determine the weight corresponding to the second phase model according to the performance index of the second phase model. For example, in M second phase models, if the performance index of the first second phase model is greater than the performance index of the M-th second phase model, the second prediction module 122 may determine the weight w2(1) is greater than the weight w2(M). The performance index may correspond to a parameter in a confusion matrix, such as accuracy, precision, a recall rate, a false positive, or an F1 score.

$$S2 = \sum_{j=1}^{M} \overline{p2(j)} * w2(j) \quad (3)$$

$$\overline{p2(i,j)} = \frac{\sum_{i=1}^{Y} p2(i,j)}{Y} \quad (4)$$

In step S209, the second prediction module 122 may select the second data subset corresponding to the second subset from the Y pieces of ECG data in response to each one in the second subset of the second probability vectors (including one or more second probabilities included in the second probability vectors) being greater than a second threshold. When there are multiple second probability vectors, the second prediction module 122 may calculate the average second probability vector according to the multiple second probability vectors, and may select the second data subset corresponding to the second subset from the Y pieces of ECG data in response to each one in the second subset of the average second probability vectors (including one or more average second probabilities included in the average second probability vector) being greater than the second threshold.

For example, if the second threshold is 20%, and Z of the Y second probabilities of the second probability vectors are greater than 20%, where Z may be a positive integer less than or equal to Y. Accordingly, the second prediction module 122 may select Z pieces of ECG data corresponding to the Z second probabilities from the Y pieces of ECG data as the second data subset.

In step S210 and step S211, the third prediction module 123 may generate at least one third probability vector corresponding to at least one third phase model according to the second data subset (i.e., the Z pieces of ECG data) and the at least one third phase model. The at least one third probability vector may include Z third probabilities corresponding to the second data subset.

Specifically, in step S210, the third prediction module 123 may input the second data subset (i.e., the Z pieces of ECG data) into K third phase models, where K may be any positive integer. Then, in step S211, the K third phase models may generate K third probability vectors according to the second data subset. Each of the K third probability vectors may include Z third probabilities respectively corresponding to the Z pieces of ECG data.

The third phase model may be adapted to determine the probability of the blockage of the specific coronary artery in a specific position according to the ECG data. For example, the third phase model may determine the probability of a blockage of the anterior, middle, or posterior parts of the left main coronary artery according to the ECG data. Note that the specific position is not limited to the anterior, middle, or posterior parts of the left main coronary artery. After a piece of ECG data is input to the third phase model, the third phase model may output a third probability corresponding to the piece of ECG data. The third probability may represent the probability of the blockage of the specific coronary artery in the specific position.

For example, the third phase model is a machine learning algorithm. For example, the machine learning algorithm corresponds to an algorithm, such as a random forest (RF) algorithm, a support vector machine (SVM) algorithm, an extreme gradient boosting (XGBoost) algorithm, or a deep learning algorithm, etc., but the disclosure is not limited thereto. For example, the deep learning algorithm corresponds to an algorithm, such as a convolutional neural network (CNN) algorithm or a long short-term memory (LSTM) algorithm, but the disclosure is not limited thereto.

In an embodiment, the third prediction module 123 may train the third phase model according to multiple pieces of training data. Each of the multiple pieces of training data may include ECG data and a label indicating whether the specific coronary artery in the specific position of the subject is blocked. Specifically, the third prediction module 123 may perform a baseline wandering removal, a noise removal, and a wavelet transform on the multiple pieces of training data to generate multiple pieces of third corrected training data. Then, the third prediction module 123 may train the third phase model according to the multiple pieces of the third corrected training data.

In an embodiment, the third prediction module 123 may perform the baseline wandering removal on the multiple pieces of training data according to a cubic spline smoothing algorithm.

In an embodiment, the third prediction module 123 may perform the noise removal on the multiple pieces of training data according to a Butterworth filter.

In an embodiment, the third prediction module 123 may train one or more features in the training data to train the third phase model. For example, one or more features are associated with a P wave, a Q wave, a R wave, an S wave, or a T wave. For example, the features may include the standard deviation of the RR interval calculated from the R wave or the slope of the ST wave calculated from the S wave and the T wave, and the like, but the disclosure is not limited thereto.

In step S212, the third prediction module 123 may generate a third determined result according to the K third probability vectors. The output module 124 may output the third determined result through the transceiver 130. The third determined result may include a probability S3 of the blockage of the specific coronary artery in the specific position of the subject.

In an embodiment, the third prediction module 123 may calculate the probability S3 of the blockage of the specific coronary artery in the specific position according to the following formula (5) and formula (6), where p3(i,j) is the i-th third probability in the j-th third probability vector in the K third probability vectors, and w3(j) is the weight of the j-th third phase model corresponding to the K third phase models. The third prediction module 123 may determine the weight corresponding to the third phase model according to the performance index of the second phase model. For example, in K third phase models, if the performance index of the first third phase model is greater than the performance index of the K-th third phase model, the third prediction module 123 may determine the weight w3(1) is greater than the weight w3(K). The performance index may correspond to a parameter in a confusion matrix, such as accuracy, precision, a recall rate, a false positive, or an F1 score.

$$S3 = \sum_{j=1}^{K} \overline{p3(j)} * w3(j) \quad (5)$$

$$\overline{p3(i, j)} = \frac{\sum_{i=1}^{Z} p3(i, j)}{Z} \quad (6)$$

The electrocardiogram may correspond to a variety of different leads. For example, the electrocardiogram may correspond to leads I, II, III, aVL, aVF, aVR, V1, V2, V3, V4, V5, or V6. In some embodiments, the electronic device 100 may generate the first determined result, the second determined result, or the third determined result according to an electrocardiogram of a variety of different leads.

Figure 3:
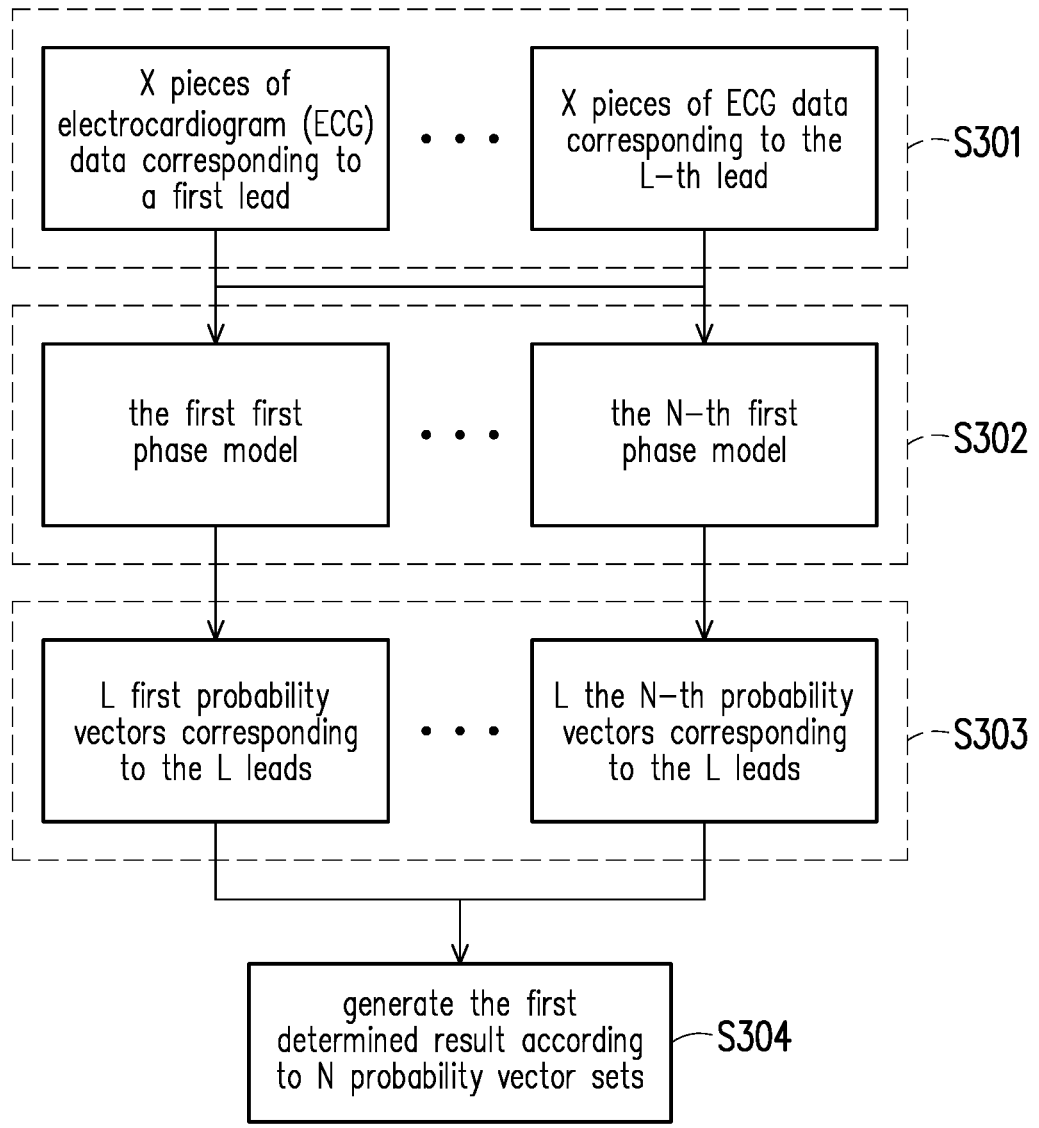
FIG. 3 illustrates a flowchart of a method for generating a first determined result according to an electrocardiogram of multiple leads according to an embodiment of the disclosure.

FIG. 3 illustrates a flowchart of a method for generating a first determined result according to an electrocardiogram of multiple leads according to an embodiment of the disclosure, and the method may be implemented by the electronic device 100 as shown in FIG. 1.

In step S301, the electronic device 100 may receive L ECG data sets corresponding to L leads through the transceiver 130. Each of the L ECG data sets may include X pieces of ECG data, where L and X may be any positive integer. For example, the electronic device 100 may receive an ECG data set corresponding to a first lead through the transceiver 130 and an ECG data set corresponding to a second lead through the transceiver 130.

In step S302, the first prediction module 121 may input the L ECG data sets into at least one first phase model respectively. For example, the first prediction module 121 may input the ECG data set corresponding to the first lead into the N first phase models, and may input the ECG data set corresponding to the L-th lead into the N first phase models, where N may be any positive integer.

In step S303, each of the N first phase models may generate L probability vectors corresponding to the L leads respectively, where each of the L probability vectors may include X probabilities corresponding to X pieces of ECG data respectively. For example, the first phase model may generate L first probability vectors, and each of the L first probability vectors may include the X probabilities corresponding to X pieces of ECG data, respectively. The N-th first phase model may generate L the N-th probability vectors, and each of the L N-th probability vectors may include the X probabilities corresponding to X pieces of ECG data, respectively.

In step S304, the first prediction module 121 may generate the first determined result according to N probability vector sets. Each of the N probability vector sets may include the L probability vectors corresponding to the L leads respectively. The N probability vector sets respectively may be the output of the N first phase models in step S303.

Figure 4:
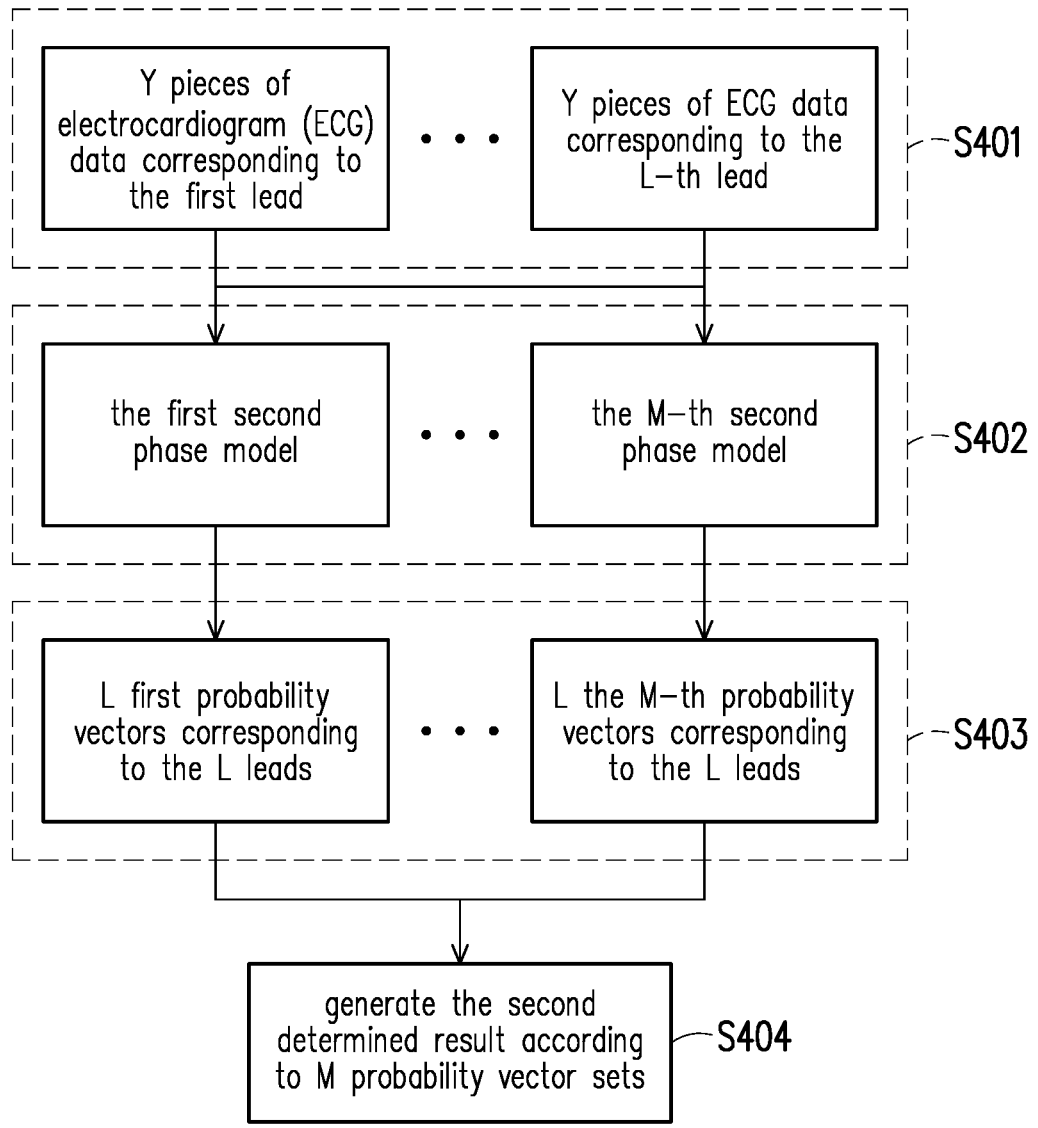
FIG. 4 illustrates a flowchart of a method for generating a second determined result according to an electrocardiogram of multiple leads according to an embodiment of the disclosure.

FIG. 4 illustrates a flowchart of a method for generating a second determined result according to an electrocardiogram of multiple leads according to an embodiment of the disclosure, and the method may be implemented by the electronic device 100 as shown in FIG. 1.

In step S401, the electronic device 100 may receive the L ECG data sets corresponding to the L leads through the transceiver 130. Each of the L ECG data sets may include Y pieces of ECG data, where L and Y may be any positive integer.

In an embodiment, each of the L ECG data sets may include X pieces of ECG data, as described in step S301. The first prediction module 121 may select the Y pieces of ECG data from the X pieces of ECG data included in each of the L ECG data sets according to the method shown in step S205, and delete the ECG data not selected, where Y may be a positive integer less than or equal to X.

In step S402, the second prediction module 122 may input the L ECG data sets into at least one second phase model respectively. For example, the second prediction module 122 may input the ECG data sets corresponding to the first lead into M second phase models, and may input the ECG data set corresponding to the L-th lead into the M second phase models, where M may be any positive integer.

In step S403, each of the M second phase models may generate the L probability vectors corresponding to the L leads. Each of the L probability vectors may include Y probabilities corresponding to X pieces of ECG data respectively. For example, the first second phase model may generate L first probability vectors, and each of the L first probability vectors may include Y probabilities corresponding to Y pieces of ECG data, respectively. The M-th second phase model may generate L M-th probability vectors, and each of the L M-th probability vectors may include Y probabilities corresponding to Y pieces of ECG data, respectively.

In step S404, the second prediction module 122 may generate the second determined result according to M probability vector sets. Each of the M probability vector sets may include the L probability vectors corresponding to the L leads. The M probability vector sets respectively may be the output of the M second phase models in step S403.

Figure 5:
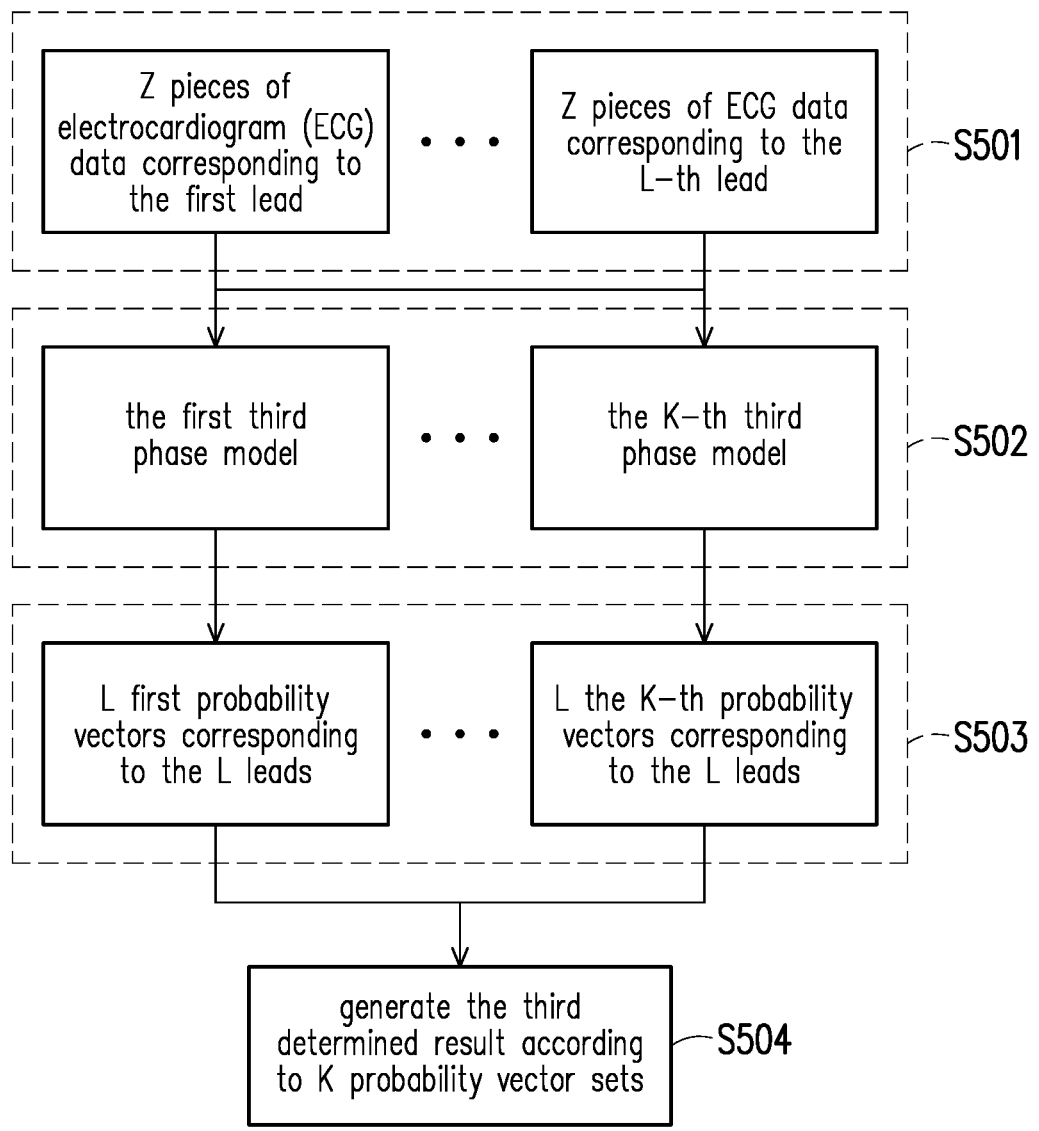
FIG. 5 illustrates a flowchart of a method for generating a third determined result according to an electrocardiogram of multiple leads according to an embodiment of the disclosure.

FIG. 5 illustrates a flowchart of a method for generating a third determined result according to an electrocardiogram of multiple leads according to an embodiment of the disclosure, and the method may be implemented by the electronic device 100 as shown in FIG. 1.

In step S501, the electronic device 100 may receive the L ECG data sets corresponding to the L leads respectively through the transceiver 130. Each of the L ECG data sets may include Z pieces of ECG data, where L and Y may be any positive integer.

In an embodiment, each of the L ECG data sets may include Y pieces of ECG data, as described in step S401. The third prediction module 123 may select Z pieces of ECG data from the Y pieces of ECG data included in each of the L ECG data sets according to the method shown in step S207, and delete the ECG data not selected, where Z may be a positive integer less than or equal to Y.

In step S502, the third prediction module 123 may input the L ECG data sets into at least one third phase model respectively. For example, the third prediction module 123 may input the ECG data set corresponding to the first lead into K third phase models, and may input the ECG data set corresponding to the L-th lead into the K third phase models, where K may be any positive integer.

In step S503, each of the K third phase models may generate L probability vectors corresponding to L leads. Each of the L probability vectors may include Z probabilities corresponding to Z pieces of ECG data respectively. For example, the first third phase model may generate L first probability vectors, and each of the L first probability vectors may include Z probabilities corresponding to Z pieces of ECG data, respectively. The K-th third phase model may generate L the K-th probability vectors, and each of the L K-th probability vectors may include Z probabilities corresponding to Z pieces of ECG data, respectively.

In step S504, the third prediction module 123 may generate the third determined result according to the K probability vector sets. Each of the K probability vector sets may include L probability vectors corresponding to the L leads. The K probability vector sets respectively may be the output of the K third phase models in step S503.

Figure 6:
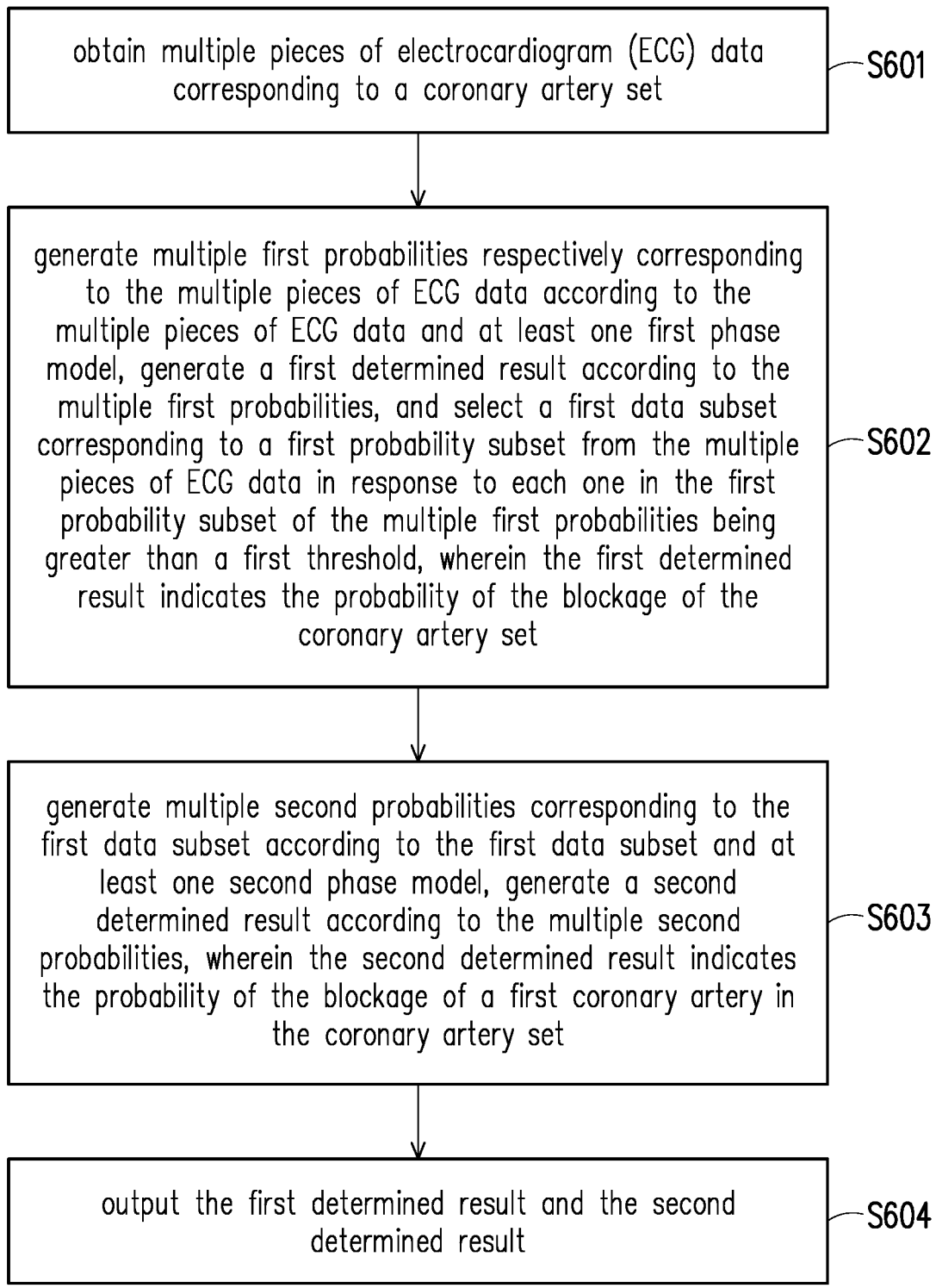
FIG. 6 illustrates a flowchart of a method for predicting a blockage of a coronary artery according to another embodiment of the disclosure.

FIG. 6 illustrates a flowchart of a method for predicting a blockage of a coronary artery according to another embodiment of the disclosure, and the method may be implemented by the electronic device 100 as shown in FIG. 1.

In step S601, multiple electrocardiogram (ECG) data corresponding to the coronary artery set are obtained. In step S602, multiple first probabilities respectively corresponding to the multiple pieces of electrocardiogram data are generated according to the multiple pieces of electrocardiogram data and at least one first phase model, a first determined result is generated according to the multiple first probabilities, and a first data subset corresponding to a first probability subset is selected from the multiple pieces of electrocardiogram data in response to each one in the first probability subset of the multiple first probabilities being greater than the first threshold, and the first determined result indicates the probability of the blockage of the coronary artery set. In step S603, multiple second probabilities corresponding to the first data subset are generated according to the first data subset and the at least one second phase model, a second determined result is generated according to the multiple second probabilities, and the second determined result indicates the probability of the blockage of a first coronary artery in the coronary artery set. In step S604, the first determined result and the second determined result are output.

Based on the above, in the disclosure, one or more machine learning algorithms are adopted to determine whether there is a blockage risk of the coronary artery set including the left main coronary artery, the left anterior descending (LAD) artery, the left circumflex artery, and the right coronary artery. If there is the blockage risk of the coronary artery set, in the disclosure, one or more machine learning algorithms are further adopted to predict which coronary artery in the coronary artery set is blocked. After confirming the type of the blocked coronary artery, one or more machine learning algorithms are further adopted to predict the precise position of the blocked coronary artery in the disclosure.

What is claimed is:

1. An electronic device for predicting a blockage of a coronary artery, comprising:
a transceiver receiving signals, in at least one of a wireless manner and a wired manner, the signals representing a plurality of electrocardiogram (ECG) data from a plurality of ECG leads applied to a patient, the ECG data corresponding to a coronary artery set, the transceiver configured to at least one of filter and amplify the signals;
a storage medium storing a plurality of modules; and
a processor coupled to the storage medium and the transceiver and accessing and executing the plurality of the modules, wherein the plurality of the modules comprise:
a first prediction module, wherein according to the plurality of the electrocardiogram data and at least one first phase model, at least one first probability vector corresponding to the at least one first phase model is generated, a first determined result is generated according to the at least one first probability vector, and in response to each one in a first subset of the at least one first probability vector being greater than a first threshold, a first data subset corresponding to the first subset from the plurality of the electrocardiogram data is selected, wherein the first determined result indicates a probability of a blockage of the coronary artery set, wherein the at least one first phase model and the at least one second phase model correspond to a machine learning algorithm executed by the processor, wherein the first determined result is determined according to a first product of at least one first average element value corresponding to the at least one first probability vector and at least one first weight, wherein the at least one first weight is associated with a performance index of the at least one first phase model;
a second prediction module, wherein according to the first data subset and at least one second phase model, at least one second probability vector corresponding to the at least one second phase model is generated, and a second determined result is generated according to the at least one second probability vector, wherein the second determined result indicates a probability of a blockage of a first coronary artery in the coronary artery set, wherein the first coronary artery comprises at least one of a left main coronary artery, a left anterior descending (LAD) artery, a left circumflex (LCX) artery, and a right coronary artery; and
an output module outputting the first determined result and the second determined result through the transceiver.

2. The electronic device according to claim 1, wherein the second prediction module selects a second data subset corresponding to a second subset from the first data subset in response to each one in the second subset of the at least one second probability vector being greater than a second threshold, wherein the plurality of the modules further comprise:
a third prediction module, wherein at least one third probability vector corresponding to at least one third phase model is generated according to the second data subset and the at least one third phase model, and a third determined result is generated according to the at least one third probability vector, wherein the third determined result indicates a probability of a first blockage position of the first coronary artery, wherein the at least one third phase model correspond to a machine learning algorithm;
wherein the output module outputs the third determined result through the transceiver.

3. The electronic device according to claim 2,
wherein the transceiver receives a plurality of second electrocardiogram data corresponding to the coronary artery set, wherein the plurality of the electrocardiogram data correspond to a first lead, wherein the plurality of the second electrocardiogram data correspond to a second lead,
wherein the first prediction module generates at least one fourth probability vector corresponding to the at least one first phase model according to the plurality of the second electrocardiogram data and the at least one first phase model, and the first determined result is generated according to the at least one first probability vector and the at least one fourth probability vector.

4. The electronic device according to claim 3,
wherein the first prediction module selects a fourth data subset corresponding to a fourth subset from the plurality of the second electrocardiogram data in response to each one in the fourth subset of the at least one fourth probability vector being greater than the first threshold,
wherein the second prediction module generates at least one fifth probability vector corresponding to the at least one second phase model according to the fourth data subset and the at least one second phase model, and the second determined result is generated according to the at least one second probability vector and the at least one fifth probability vector.

5. The electronic device according to claim 4,
wherein the second prediction module selects a fifth data subset corresponding to a fifth subset from the fourth data subset in response to each one in the fifth subset of the at least one fifth probability vector being greater than the second threshold,
wherein the third prediction module generates at least one sixth probability vector corresponding to the at least one third phase model according to the fifth data subset and the at least one third phase model, and the third determined result is generated according to the at least one third probability vector and the at least one sixth probability vector.

6. The electronic device according to claim 1,
wherein the first prediction module performs a baseline wandering removal, a noise removal, and a wavelet transform on a plurality of training data to generate a plurality of first corrected training data, and the at least one first phase model is trained according to the plurality of the first corrected training data.

7. The electronic device according to claim 6, wherein the first prediction module trains the at least one first phase model according to at least one feature, wherein the at least one feature is associated with at least one as follows:
a P wave, a Q wave, a R wave, an S wave, and a T wave.

8. A method for predicting a blockage of a coronary artery, comprising:
receiving signals, via a transceiver, in at least one of a wireless manner and a wired manner, the signals representing a plurality of electrocardiogram (ECG) data from a plurality of ECG leads applied to a patient, the ECG data corresponding to a coronary artery set;
at least one of filter and amplify the signals to obtain the plurality of ECG data;
generating at least one first probability vector corresponding to at least one first phase model according to the plurality of the electrocardiogram data and the at least one first phase model, generating a first determined result according to the at least one first probability vector, and selecting a first data subset corresponding to a first subset from the plurality of the electrocardiogram data in response to each one in the first subset of the at least one first probability vector being greater than a first threshold, wherein the first determined result indicates a probability of a blockage of the coronary artery set, wherein the at least one first phase model corresponds to a machine learning algorithm executed by a processor, wherein the first determined result is determined according to a first product of at least one first average element value corresponding to the at least one first probability vector and at least one first weight, wherein the at least one first weight is associated with a performance index of the at least one first phase model;
generating at least one second probability vector corresponding to at least one second phase model according to the first data subset and the at least one second phase model, and generating a second determined result according to at least one second probability vector, wherein the second determined result indicates a probability of a blockage of a first coronary artery in the coronary artery set, wherein the first coronary artery comprises at least one of a left main coronary artery, a left anterior descending (LAD) artery, a left circumflex (LCX) artery, and a right coronary artery; and
outputting, via the transceiver, the first determined result and the second determined result.

9. A non-transitory computer readable storage media encoded with instructions that, when executed by a processor cause the processor to:

receive, via a transceiver, in at least one of a wireless manner and a wired manner, a plurality of electrocardiogram (ECG) data from a plurality of ECG leads applied to a patient, the ECG data corresponding to a coronary artery set;

generate at least one first probability vector corresponding to at least one first phase model according to the plurality of the electrocardiogram data and the at least one first phase model, generate a first determined result according to the at least one first probability vector, and select a first data subset corresponding to a first subset from the plurality of the electrocardiogram data in response to each one in the first subset of the at least one first probability vector being greater than a first threshold, wherein the first determined result indicates a probability of a blockage of the coronary artery set, wherein the at least one first phase model corresponds to a machine learning algorithm executed by a processor, wherein the first determined result is determined according to a first product of at least one first average element value corresponding to the at least one first probability vector and at least one first weight, wherein the at least one first weight is associated with a performance index of the at least one first phase model;

generate at least one second probability vector corresponding to at least one second phase model according to the first data subset and the at least one second phase model, and generate a second determined result according to at least one second probability vector, wherein the second determined result indicates a probability of a blockage of a first coronary artery in the coronary artery set, wherein the first coronary artery comprises at least one of a left main coronary artery, a left anterior descending (LAD) artery, a left circumflex (LCX) artery, and a right coronary artery; and output, via the transceiver, the first determined result and the second determined result.

* * * * *